(12) United States Patent
Lloyd et al.

(10) Patent No.: US 7,972,614 B2
(45) Date of Patent: *Jul. 5, 2011

(54) DUAL-ACTION PEST CONTROL FORMULATION AND METHOD

(75) Inventors: Jeffrey Douglas Lloyd, Rockford, TN (US); John Murphy, Rockford, TN (US); David Ashley Ezell, Rockford, TN (US)

(73) Assignee: Nisus Corporation, Rockford, TN (US)

( * ) Notice: Subject to any disclaimer, the term of this patent is extended or adjusted under 35 U.S.C. 154(b) by 625 days.

This patent is subject to a terminal disclaimer.

(21) Appl. No.: 11/279,459

(22) Filed: Apr. 12, 2006

(65) Prior Publication Data

US 2007/0240360 A1    Oct. 18, 2007

(51) Int. Cl.
*A01N 25/34* (2006.01)

(52) U.S. Cl. ........ 424/410; 424/405; 424/408; 424/409; 424/658; 424/659; 424/84; 514/427

(58) Field of Classification Search .................. None
See application file for complete search history.

(56) References Cited

U.S. PATENT DOCUMENTS

| | | | |
|---|---|---|---|
| 4,287,183 A | 9/1981 | Hagerman et al. | |
| 4,518,580 A | 5/1985 | Pasarela | |
| 4,581,378 A | 4/1986 | Lazar et al. | |
| 5,104,664 A | 4/1992 | Palmere et al. | |
| 5,296,240 A | 3/1994 | Palmere et al. | |
| 5,592,774 A | 1/1997 | Galyon | |
| 5,676,960 A * | 10/1997 | Myles | 424/410 |
| 6,007,832 A * | 12/1999 | Stapleton | 424/410 |
| 6,368,529 B1 | 4/2002 | Manning et al. | |
| 6,426,095 B2 | 7/2002 | Palmere et al. | |
| 6,630,174 B2 | 10/2003 | Palmere et al. | |
| 6,645,949 B1 * | 11/2003 | Nigg et al. | 514/64 |
| 6,689,796 B1 | 2/2004 | Johnson et al. | |
| 6,896,908 B2 | 5/2005 | Lloyd et al. | |
| 6,984,662 B2 | 1/2006 | Cottrell et al. | |
| 7,067,142 B2 * | 6/2006 | Yonker et al. | 424/406 |
| 7,163,974 B2 | 1/2007 | Manning et al. | |
| 7,223,415 B1 | 5/2007 | Malone et al. | |
| 7,264,827 B1 * | 9/2007 | Malone et al. | 424/658 |
| 2003/0215481 A1 | 11/2003 | Borchert | |
| 2004/0259836 A1 * | 12/2004 | Twydell | 514/53 |
| 2005/0196628 A1 | 9/2005 | Lloyd et al. | |
| 2006/0045898 A1 | 3/2006 | Lloyd et al. | |
| 2006/0057178 A1 * | 3/2006 | Borchert et al. | 424/408 |

OTHER PUBLICATIONS

Genesis Labroatories, Inc. Wellington, CO. Standard House Mouse Acute Dry Bait Laboratory Test Method, OPP Designation. 1:210 Revision No. 9 USEPA—"EPA Challenge Diel" date unknown.
ANON 1989 Merck Index, An Encyclopedia of Chemicals, Drugs and Biologicals), 11th Edition, Budavari S (ed) Merck & Co, Inc.
Williams D F (1990) "Effects of Fenoxycarb Baits on Laboratory Colonies of the Pharaohs Ant Monomorium Pharaonis". In Applied Myrmecology—A World Perspective '676-683. Ed Jaffe K. & Cedeno A Westview Press San Francisco & Oxford.

* cited by examiner

*Primary Examiner* — Neil Levy
(74) *Attorney, Agent, or Firm* — Luedeka, Neely & Graham, P.C.

(57) ABSTRACT

The present disclosure provides a dual-action pest control formulation for controlling rodents and arthropods, the formulation including: a rodenticide; an insecticide; an optional attractant; and a carrier matrix. The present disclosure also provides a method of controlling rodents and arthropods, the method including: applying the dual action pest formulation to a target area.

18 Claims, No Drawings

DUAL-ACTION PEST CONTROL FORMULATION AND METHOD

BACKGROUND

Rodents, such as mice and rats, are common pests that can cause significant damage to property and products, and can be disease carriers. Similarly, arthropods, such as insects including roaches and ants, can cause considerable property damage and can also be disease carriers. Rodents and insects can often coexist in the same environment, and many environments having a rodent infestation also have an insect infestation.

Despite the coexistence of rodents and insects, traditional pest control generally involves a separate treatment for attempting to control each pest. When traditional pest control formulations are set out, the types of active ingredients used to control one type of organism are typically different from those that will work for another type of organism. For example, bromadiolone is a common active ingredient for control of rodents, but it has no insecticidal properties. Similarly, pyrethroids are good examples of insecticides that have no rodenticidal performance.

The exclusive nature of these active ingredients can be problematic. For example, rodenticides may be consumed by roaches before rodents have a chance to consume them. In such situations, the roach population increases and there is no impact on the rodent population, so the infestation of both populations can actually become worse than it was prior to the attempted pest control intervention. The converse is also possible. Insect bait systems can attract and increase rodent populations because they are not harmful to rodents, and this results in both insect and rodent pest populations proliferating.

Therefore, a need exists for improved pest control formulations having dual-action properties.

SUMMARY

The disclosure relates to materials and methods for controlling rodent and insect pests. In particular, the disclosure relates to a dual-action pest control formulation having at least two active pesticidal ingredients, and preferably being resistant to mold formation and biodeterioration.

The present disclosure is directed to a pest control composition formulated to be attractive to, and consumed by, a range of rodent and arthropod (including insect) pest species. The physical and chemical formulation provides a rodent and insect bait with broad spectrum performance against numerous rodent pests, such as rats and mice, and most insect pests, as well as many general non-insect arthropod pests. The inventive formulation effectively prevents the problems of a single-target pest control substance being consumed by a non-target specie, resulting in promoting a non-target specie at the expense of the efforts to exterminate the targeted specie.

The present disclosure, in embodiments, provides dual-action pest control formulations which include both an insecticide and a rodenticide to kill both rodents and insects, and permits various target pests to simultaneously consume a toxic dose of the pest control formulation. In embodiments, the insecticide is preferably a borate. The present disclosure also preferably provides a pest control formulation that maintains effectiveness after exposure to high humidity because it reduces mold growth and other biodeterioration that would otherwise inhibit consumption of the formulation by rodent and arthropod pests. The disclosure also provides dual-action pest control formulations which offers a potential human health benefit over rodenticides used in a home or within an enclosed environment by limiting exposure to mold and mold spores.

The pest control formulation of the present disclosure generally combines the following specific components: a rodenticide or rodenticidal active ingredient that is non-repellent to insects and rodents, and an insecticide or insecticidal active ingredient in an amount that is non-repellent to rodents and insects. The insecticide desirably also serves as a rodent attractant, and can include a borate salt or another suitable borate such as boric acid. The formulation can also include a solid, a liquid, or granular carrier matrix, and one or more food attractants that serve to invite ingestion of the entire matrix and the active ingredients by both rodent and insect pests. Suitable attractants can include, for example, any of mixed carbohydrates (including sugars), lipids, proteins, and combinations thereof.

More broadly, the disclosure includes a dual-action pest control formulation for controlling rodents and arthropods, the formulation comprising a rodenticide, an insecticide, and a carrier matrix. The rodenticide can be, for example, a single dose anti-coagulant. This rodenticide is typically substantially non-repellent to rodents and insects. Suitable rodenticides include, for example, brodifacoum, bromadiolone, difethialone, warfarin, chlorophacinone, diphacinone, zinc phospide, bromethalin, and like compounds, or combinations thereof. Two particularly useful rodenticides are, for example, difethialone and bromadiolone.

Similarly, the insecticidal active ingredient is desirably substantially non-repellent to both rodents and insects. The insecticidal active ingredient can include, for example, one or more of pyriproxyfen, methoprene, fenoxycarb, hydramethylnon, sulfluramid, fipronil, abamectin, propoxur, spinosad, and like compounds, or mixtures thereof. In embodiments, the insecticide comprises an insect growth regulator.

Borates are particularly useful insecticides, and borax (sodium borate) is an especially useful insecticide. In embodiments, the insecticidal active ingredient can comprise, for example, less than about 20 percent borax based upon total dry weight of the formulation, and in other embodiments, less than about 10 percent. Typically, when borax is used, it comprises greater than about 2 percent based upon total weight of the formulation. Lower levels of borates tend to result in less resistance to mold formation in the finished formulation. In embodiments, the percentage of borax can be, for example, from about 3 to about 8 percent by weight of the formulation.

The formulation can also generally include a carrier matrix. Suitable carrier matrices include, for example, ground corn cobs, or like particulate materials derived from corn cobs, waxes, or other like organic materials. The formulation can also, in embodiments, include at least one attractant. In general, the attractant can include, for example, a carbohydrate, a lipid, or a protein. In embodiments, the attractant and the matrix can be the same material. In embodiments, the attractant and the matrix can be different or dissimilar materials.

The present disclosure is also directed to a method for controlling rodents and arthropods (including insects). In embodiments, the method comprises providing a dual-action pest control formulation which is both attractive and lethal for rodents and insects, the formulation comprising a rodenticide that is substantially non-repellent to rodents and insects, and an insecticide that is substantially non-repellent to rodents and insects. The insecticide can comprise, for example, from about 2 to about 20 percent borax based upon the total dry weight of the pest control formulation and a carrier matrix. The rodenticide of the formulation can be, for example, difethialone, bromadiolone, and like compounds, or combinations thereof. In embodiments, the insecticide can comprise generally less than about 20 percent borax, and often less than about 10 percent borax, of the formulation by dry weight. In embodiments, the insecticide can comprise, for example, from about 3 to about 8 percent borax.

DETAILED DESCRIPTION

The present disclosure is directed to a formulation that is preferably attractive to, and consumed by, a range of rodent and arthropod pest species, including insects. The formulation also preferably maintains its attractiveness to rodents even after prolonged exposure to high humidity. The formulation kills the pests, and in so doing, removes their nuisance and disease carrying potential from the treated environment. The formulation provides a superior rodent and insect bait with broad-spectrum performance against numerous rodent pests, such as rats and mice, and most insect pests, as well as many general non-insect arthropod pests. The formulation can be used against rats or mice, and generally controls rodent infestation. In addition, the formulation preferably limits mold growth and has reduced susceptibility to becoming rancid, while still being palatable and attractive to rodents. Formulations of the disclosure retard mold growth in the formulation that can typically occur at high humidity. Mold growth is known to have anti-feedant properties, which properties results in decreased consumption and reduced rodent kill rates, arthropod or insect kill rates, or both. Thus, the present disclosure provides a pest control formulation and method for controlling rodents and arthropods, which formulation and method are expected to have enhanced pest control performance following enhanced consumption of rodent and arthropod active ingredients.

The present formulation effectively limits and prevents the problem in which a single-target pest control substance is consumed by a non-target specie, resulting in promoting this non-target specie at the expense of the efforts to exterminate the targeted specie. The formulation also helps to limit mold and bacterial growth, which can significantly diminish a bait's attractiveness to rodents.

The formulation of the present disclosure generally combines the following specific components: a rodenticide that is non-repellent to insects and rodents, and an insecticide in an amount that is non-repellant to rodents and insects. The insecticide desirably serves as a rodent attractant, and can include, for example, a borate or borate salt, such as boric acid, or mixtures thereof. The formulation can also include a solid, liquid, or granular carrier matrix and one or more attractants that serve to invite ingestion of the entire matrix and the active ingredients by both rodent and insect pests. Suitable attractants include, for example, mixed carbohydrates including, for example, complex and simple sugars, lipids, proteins, and mixtures thereof.

Various aspects of the invention will now be described in detail.

Rodenticide

Many rodenticides can be used to practice the present invention, including, for example, brodifacoum, bromadiolone, difethialone, warfarin, chlorophacinone, diphacinone, zinc phospide, bromethalin, and like compounds, or mixtures thereof. A preferred rodenticide is, for example, a single dose anticoagulant, for which Vitamin K1 is a readily available antidote in case of accidental human or pet ingestion. The rodenticide can also be a multiple dose anticoagulant. Two particularly useful rodenticides are, for example, difethialone and bromadiolone. These rodenticides are desirable, in part, because they are effective against both rats and mice.

The rodenticide is desirably substantially non-repellant to rodents and insects. A rodenticide is substantially non-repellant to rodents and insects where most rodents and insects will consume at least some of a composition containing the rodenticide. Other rodenticides are known and include, for example, poisons such as arsenic, barium, barium carbonate, bromethalin, strychnine, tetramine, or thallium. Still other rodenticides include non-repellent non-anticoagulant compounds, such as disclosed in U.S. Pat. No. 6,689,796, and more recently sperm-count lowering or sterilant compounds. U.S. Pat. No. 4,287,183, to Hagerman et al., entitled "Method for Killing Rodents," mentions a rodenticide composition comprising a dry mixture of a first ingredient which is a substance that rodents are fond of eating (e.g., cornmeal), and a second ingredient which has the propensity to react with water and thereby transform to a hydrated cementitious solid aggregate (e.g., plaster of paris). The disclosures of these U.S. Patents are incorporated herein by reference in their entirety.

Insecticide

Various insecticides may be used in accordance with the present disclosure, and include, for example, various insect growth regulators. The insecticide desirably can be substantially non-repellent to both rodents and insects, and desirably can be relatively slow acting. The insecticide selected can include, for example, a stomach poison, contact insecticide, insect growth regulator, and like insecticides, or combinations thereof, for example, one or more of pyriproxyfen, methoprene, fenoxycarb, hydramethylnon, sulfluramid, fipronil, abamectin, propoxur, spinosad, or mixtures thereof. In embodiments, the insecticide can comprise an insect growth regulator, such as hyrdroprene, pyriproxyfen, fenoxycarb, or combinations thereof. The insecticide is preferably of a sufficient concentration to realize insecticidal properties.

Borates are particularly useful insecticides, and borax is an especially useful borate example. When borax is used, the pest control composition generally can comprise less than about 20 percent by weight borax based upon total dry weight of the formulation, and in embodiments less than about 10 percent by weight. Typically, when borax is used, the formulation can comprise greater than about 1 percent borax based upon total dry weight of the formulation. In embodiments, the percentage of borax can be, for example, from about 3 to about 8 percent by dry weight of the total formulation. For example, the insecticide may comprise borax pentahydrate, borax decahydrate, disodium octaborate tetrahydrate, boric acid, calcium borate, zinc borate, sodium calcium borate, and like borates, or mixtures thereof. The borate content can be, for example, from about 2% to about 10% boric acid equivalent loading of boric acid, borax or disodium octaborate tetrahydrate (DOT) on a dry weight percent basis (by comparing $B_2O_3$ content).

The insecticide should be substantially non-repellant to rodents and insects. An insecticide is substantially non-repellant to rodents and insects where most rodents and insects will consume at least some of a composition containing the insecticide. U.S. Pat. No. 6,984,662, to Cottrell, et al., entitled "High Concentration Topical Insecticide Containing Insect Growth Regulator," mentions an insecticide formulation that contains both an insecticide and an insect growth regulator, the disclosure of which is incorporated herein by reference in its entirety.

Attractants

The pest control formulation can also optionally include one or more attractants. Lipids and carbohydrates are two particularly useful attractants used in the formulation of the disclosure. Two or more attractants or food sources within the formulation can be used to give the formulation a broader appeal by satisfying a variety of nutritional needs of various target pests. The use of two or more pest active ingredients along with multiple attractants together can provide synergistic performance in terms of total pest management. Many attractants are suitable and include, for example, oil, sugar, protein sources (e.g., yeast extract, soy, albumin, etc.), and carbohydrate sources (e.g., wheat, corn, oat, rice or potato flour, malt extract, etc.). For example, various lipids, corn oil, soy bean oil, peanut oil, animal derived fat, or mixtures thereof can be suitable attractants, in embodiments. The amount of attractant included in a formulation is selected so that pest species are adequately attracted to and consume the formulation. U.S. Pat. No. 4,581,378, issued Apr. 8, 1986, to Lazar et al., entitled "Rodenticide Compositions Comprising an Artificial Sweetener and a Rodenticide," discloses a food energy inhibitor for controlling rodents, such as rats and mice, which comprises pellets of either crushed or dried corncobs, or spent grain bound together with an attractant, such as molasses, the disclosure of which is incorporated herein by reference in its entirety.

Carrier Matrix

The pest control formulation also generally includes a carrier matrix designed to give physical form and carry the attractants and active ingredients. The carrier matrix may also itself comprise an attractant. Many different carrier matrices are suitable including, for example, at least one of a flour or meal of a carbohydrate, lipid, or protein. Suitable carrier matrices can also include, for example, cellulose-based plant derived products, corn cobs, wax, corn starch, corn meal, corn flour, potato starch, potato meal, potato flour, rice or rice flour, nut meal, and like materials, or combinations thereof, or materials derived from any of these. In embodiments, the carrier matrix is blended with the other constituents of the formulation and baked, formed, or shaped to serve as a bait for the targeted pest.

The amount of carrier matrix in the formulation can be chosen so that the resulting formulation has desirable shape and mass for manufacture, packaging, handling, application, and pest consumption. For example, in one embodiment, a formulation may comprise about 80% by weight carrier matrices. U.S. Pat. No. 4,518,580, issued May 21, 1985, to Pasarela, entitled "Expanded Corncob Grits Having Increased Absorptivity and a Method for the Preparation thereof," provides an example matrix where the expanded grits, which possess increased absorptivity, are found to be useful in the formulation of insecticidal baits, especially fire ant baits, and other agricultural compositions. See also the abovementioned U.S. Pat. No. 4,581,378.. The disclosures of the above U.S. Patents are incorporated herein by reference in their entirety.

A suitable wax can be any mineral, plant, or animal derived wax substance including for example, natural wax, synthetic wax, or mixtures thereof, such as, slack wax from Exxon Corp. Other examples of suitable waxes include beeswax, paraffin wax, micro wax, microcrystalline wax, candellila wax, carnauba wax, rice wax, montan wax, polyethylene wax, polypropylene wax, copolyalkylene wax, oxidized polyalkylene wax, poly(alkylene oxide) wax, copoly(alkylene oxide) wax, and like substances, or mixtures thereof.

The use of two or more active ingredients provides the bait with a broader spectrum of performance. The use of multiple actives and multiple attractants provides synergistic performance in overall pest management.

EXAMPLE 1

Example Formulation. One illustrative formulation for pest control consists of about 39% by weight slack wax (available from Exxon) and about 30% ground corncob as a carrier matrix, about 10% corn oil and about 15% sugar as attractants, about 5% borax as an insecticide, and about 0.005% bromadiolone as a rodenticide, based on the total weight of the formulation.

The components can be blended together in an essentially dry process that intimately combines the components to produce specific sized granules that can perform in pest (rodent and arthropod) abatement for extended time periods, for example, from about 1. to about 12. months, or longer. The powdered sugar, borate and bromadiolone are added to the corn cob and pre-mixed in a Marion mixer ribbon blended for about 5 to about 10 minutes. To this mixture is added the corn oil and wax and mixing continued for about an additional 20 to 25 minutes. Heat can optionally be applied to melt and distribute the wax as a binding agent. A wet process with an alternative binder material, for example, agar, gelatin, albumin, and like materials, or mixtures thereof, can also optionally be selected. The binder can be used to conveniently produce molded solid forms of the disclosure, such as a cake or bar, from which granules can be easily broken off from the solid form by a feeding pest.

EXAMPLE 2

EPA Diet. Yet another illustrative formulation is the EPA test formulation diet and consists of the ingredients in the amounts shown Table 1.

TABLE 1

EPA Test Formulation Diet.

| Ingredient | % by weight |
|---|---|
| Cornmeal (whole yellow ground corn) | 65 |
| Rolled oat groats (ground) | 25 |
| Sugar (10× powdered or confectioners, 95% + purity) | 5 |
| Corn oil (95% + purity) | 5 |

The EPA diet is also referred to as the "EPA challenge diet" see for example, "EPA 1991. Standard House Mouse Acute Dry Bait Laboratory Test Method. OPP Designation: 1.210 Revision No. 9. USEPA." The EPA challenge diet was prepared by Genesis Laboratories of Wellington, Colo. (www.genesislabs.com) by combining the solid ingredients, adding the corn oil, and then mixing thoroughly with utensils in vessels that were free of contamination. The diet could be readily modified further with the addition of one or more toxicants, such as described below.

Methods and Materials of Formulation and Use

In embodiments, the ingredients used to make the dual-action rodent and insect control formulation can be mixed using various methods known to those skilled in the art. It is generally desirable to mix the components in a dry process that blends and combines the components and produces specific sized granules that can perform dual-action pest control for extended time periods. Alternatively, the materials can be mixed together as a wet formulation, heated, and extruded.

Thoroughly mixing the ingredients is preferred to partial mixing. In embodiments, it is desirable that every particle of the formulation have activity against both insects and rodents. Thus, even if a particular pest preferentially selects particles of certain size, texture, or other physical characteristics, that pest will still be exterminated. If the formulation contains distinct particles that only contain one active ingredient, then one pest may selectively eat only that formulation that is not toxic to it, thereby reducing efficacy of pest control measures. Also, in some circumstances it is possible to have the particles separate from one another during shipping or packaging, due to for example particle size or density differences or sorting, thereby limiting the effectiveness of the formulation if one of the active ingredients is not readily accessible because the particles containing it have settled to the bottom of a package or application device. Although it is generally desirable that the active ingredients be combined within each individual particle, the formulation may still be effective where the active ingredients are combined within the formulation but on different individual particles in the formulation if the target pests consume a sufficient quantity of the target insecticide or rodenticide that is toxic to them.

It has been discovered that different pests sometimes require different particle sizes for the formulation to be effective. For example, insects, especially ants, sometimes prefer to consume particles of granular sizes that are within the range of about #8 Mesh to about #100 Mesh and #14 Mesh to about #80 Mesh. This particle size range has also been found to provide ample foraging opportunities for many different insect species and size ranges, such as cockroaches, silverfish, crickets, numerous species of ants (including fire ants, argentine ants, odorous house ants, carpenter ants, and pavement ants), and can still be eaten by rodents. After formulation, such as by agglomerative binding, rodents and especially insects can remove their preferred particle size from a larger solid particle with relative ease.

In embodiments, a combined sandwich approach can also be used to deliver the active ingredients of the disclosure. In such implementations, a rodenticide is formed separately from an insecticide, and then the rodenticide and the insecticide are intimately joined together to form a sandwich or layered structure. Such a physical formulation is best carried out with solid forms. Solid forms or solid formulations, such as monolith or block formation, can be accomplished in many ways known to those skilled in the art by, for example, solidifying a liquid or solidifying a granular material into an aggregate or like mass with a suitable binder, using for example, agar (available from Oxoid), animal or vegetable derived gelatin, long chain polyalkylene glycols (available from Dow Chemical), waxes, natural or synthetic resins, and like methods and materials, or combinations thereof.

The disclosure is also directed to a method of controlling rodents and insects. The method comprises providing a dual-action pest control formulation for rodents and insects, the dual-action pest control formulation comprising a rodenticide that is substantially non-repellent to rodents or insects, and an insecticide that is substantially non-repellent to rodents or insects. The insecticide can comprise from about 2 to about 20 percent borax based upon the total dry weight of the pest control formulation; and a carrier matrix. The rodenticide of the dual-action pest control formulation can be, for example, difethialone, bromadiolone, and like rodenticides, or combinations thereof.

Experimental Results

The purpose of this study was to determine the acceptance and consumption rate by laboratory mice (*Mus musculus*) of diet formulations of the disclosure having borate and comparison diet formulations free of borate, after the diet formulations had been exposed to high humidity, for example, of about 50-55% relative humidity or higher, during incubation at about 20 to about 25° C. for two months. Each of four experimental diets (Diets A-D) were formulated from the abovementioned EPA challenge diet formulation and were simultaneously presented to twelve mice and evaluated for acceptability during a 3-day diet presentation period. Diet A contained 2.5% by weight boric acid equivalent (BAE) Borax and was not exposed to high humidity. Diet B contained 2.5% BAE Borax and was exposed to high humidity. Diet C was a humidity control that contained no borate and was exposed to high humidity. Diet D was a fresh control that contained no borate and was not exposed to high humidity. Mold grew on the incubated diet formulations at elevated humidities although to different extents. The extent of mold growth appeared to depend upon the diet composition. The diets that included a borate appeared to inhibit mold growth and improved the palatability and consumption of incubated diets.

Twelve mice (6 male, 6 female) were evaluated for the test diets. Mice were housed in double-wide cages measuring 24×40.5×18 cm (L×W×H) with a floor area of least 972 cm$^2$. Tap water in glass bottles with stainless steel sipper tubes were available ad libitum. The cages were suspended from shelves on two single-sided racks. Mice were placed in cages identified by a consecutive number 1-12 and a descriptor for their sex (e.g., M or F).

The diets were modified by adding borates as indicated to the EPA challenge diet and then exposing the diets to high humidity to produce the four diets (Diets A-D). On the morning of the experimental set up, all maintenance diet rodent pellets were removed from each cage. Glass feed cups were used to present the four test diets to each mouse to determine if there was preference for any one diet. The feed cups were labeled with the cage number and treatment diet. The cups were placed along the front of the cage and the cup positions were rotated throughout the test period to prevent positional bias. The results of the acceptance test appear in Table 2.

TABLE 2

Diet acceptance test results.

| Mouse Number and Sex | Total Test Diet A (borate) Consumed (g) | Total Test Diet B (borate + humidity) Consumed (g) | Total Test Diet C (humidity) Consumed (g) | Total Test Diet D (control) Consumed (g) | Total Diet Consumed (g) |
|---|---|---|---|---|---|
| 1F | 3.2 | 9.4 | 10.0 | 18.8 | 41.4 |
| 2F | 4.3 | 4.5 | 6.6 | 26.1 | 41.5 |
| 3F | 12.1 | 12.9 | 6.7 | 14.7 | 46.4 |
| 4F | 12.3 | 7.0 | 1.8 | 12.4 | 33.5 |
| 5F | 7.6 | 4.5 | 0.0 | 16.8 | 28.9 |
| 6F | 6.5 | 12.4 | 11.4 | 22.4 | 52.7 |
| 7M | 12.8 | 17.6 | 1.0 | 13.7 | 45.1 |
| 8M | 8.4 | 20.4 | 6.2 | 20.9 | 55.9 |
| 9M | 11.0 | 0.3 | 1.5 | 14.0 | 26.8 |
| 10M | 9.9 | 1.6 | 0.3 | 6.8 | 18.6 |
| 11M | 16.1 | 1.5 | 1.0 | 14.4 | 33.0 |
| 12M | 24.3 | 5.3 | 1.8 | 13.4 | 44.8 |
| Total (g) | 128.5 | 97.4 | 48.3 | 194.4 | 468.6 |
| Percent Consumed | 27.4% | 20.8% | 10.3% | 41.5% | 100.0% |

The mice on average consumed Diet A at 27.4% of total consumption, Diet B at 20.8%, Diet C at 10.3%, and the Control Diet D at 41.5%. This study shows a statistical preference (Fisher's PLSD, p=0.05) for ambient humidity exposed and fresh bait (Diet A and Diet D) over humidity exposed bait (Diet B and Diet C). This study also shows a statistical preference (paired t-test, p=0.05) for bait formulated with borate compared to bait without borate when exposed to high humidity (Diet B and Diet C). Although not measured, the diets without a borate probably had higher mold or bacterial growth which could produce the observed anti-feedant properties.

While the present invention has been described with reference to several particular implementations, those skilled in the art will recognize that many changes may be made hereto without departing from the spirit and scope of the present invention.

We claim:

1. A dual-action pest control formulation for controlling rodents and arthropods, the formulation comprising:
   a granular formation comprising granular particles having activity against both insects and rodents, and comprising:
   a rodenticide which is substantially non-repellent to rodents and insects and includes at least bromadiolone;
   an insecticide, wherein the insecticide comprises less than about 10 percent, based upon total dry weight of the formulation, of a borate selected from the group consisting of borax pentahydrate, borax decahydrate, disodium octaborate tetrahydrate, boric acid, calcium borate, zinc borate, sodium calcium borate and mixtures thereof;
   an attractant; and
   a granular carrier matrix.

2. The dual-action pest control formulation of claim 1, wherein the rodenticide comprises a single dose anti-coagulant.

3. The dual-action pest control formulation of claim 1, wherein the granular particles have a granular size of from about #14 Mesh to about #80 Mesh.

4. The dual-action pest control formulation of claim 1, wherein the insecticide comprises greater than about 1 percent borax pentahydrate or borax decahydrate based upon total dry weight of the formulation.

5. The dual-action pest control formulation of claim 1, wherein the insecticide comprises from about 3 to about 8 percent borax pentahydrate or borax decahydrate.

6. The dual-action pest control formulation of claim 1, wherein the carrier matrix comprises a particulate of corn cob, wax, corn starch, corn meal, corn flour, potato starch, potato meal, potato flour, rice, rice flour, nut meal, or mixtures thereof.

7. The dual-action pest control formulation of claim 1, wherein the attractant comprises a carbohydrate, a lipid, a protein, or combinations thereof.

8. The dual-action pest control formulation of claim 1, wherein the insecticide is substantially non-repellent to rodents and insects.

9. The dual-action pest control formulation of claim 1, wherein the formulation inhibits mold growth and the formulation resists biodeterioration.

10. A dual-action pest control formulation in the form of a monolith or block comprising:
    a monolith or block shaped bait formulation comprising a binder and a plurality of granular particles having activity against both insects and rodents, wherein the granular particles comprise:
    a rodenticide that is substantially non-repellent to rodents and insects wherein the rodenticide comprises bromadiolone;
    an insecticide that is substantially non-repellent to rodents and insects, the insecticide comprising from about 2 to about 10 percent weight, based upon the total dry weight of the pest control formulation, of a borate selected from the group consisting of borax pentahydrate, borax decahydrate, disodium octaborate tetrahydrate, boric acid, calcium borate, zinc borate, sodium calcium borate and mixtures thereof; and
    a granular carrier matrix.

11. The dual-action pest control formulation of claim 10, wherein the insecticide comprises from about 2 to about 10 percent borax pentahydrate or borax decahydrate based upon total dry weight of the formulation.

12. The dual-action pest control formulation of claim 10, wherein the insecticide comprises from about 3 to about 8 percent borax pentahydrate or borax decahydrate.

13. The dual-action pest control formulation of claim 10, further comprising an attractant.

14. The dual-action pest control formulation of claim 13, wherein the attractant comprises mixed carbohydrates, lipids, or proteins.

15. A method of controlling rodents and insects, the method comprising: applying the dual action pest formulation of claim 10 to a target area.

16. The method of controlling rodents and insects of claim 15, wherein the insecticide comprises from about 2 to about 10 percent borax pentahydrate or borax decahydrate based upon total dry weight of the formulation.

17. The method of controlling rodents and insects of claim 15, wherein the insecticide comprises from about 3 to about 8 percent borax pentahydrate or borax decahydrate.

18. The method of controlling rodents and insects of claim 15, wherein the dual-action pest control formulation further comprises an attractant.

* * * * *